United States Patent [19]

Lesur et al.

[11] Patent Number: 5,252,587
[45] Date of Patent: Oct. 12, 1993

[54] N-DERIVATIVES OF 1-DEOXY NOJIRIMYCIN

[75] Inventors: Brigitte Lesur, Strasbourg; Jean-Bernard Ducep, Sundhoffen; Charles Danzin, Strasbourg, all of France

[73] Assignee: Merrell Dow Pharmaceuticals, Inc., Cincinnati, Ohio

[21] Appl. No.: 898,992

[22] Filed: Jun. 15, 1992

Related U.S. Application Data

[63] Continuation-in-part of Ser. No. 691,189, Apr. 25, 1991, abandoned.

[30] Foreign Application Priority Data

Apr. 27, 1990 [EP] European Pat. Off. ......... 90401169.9

[51] Int. Cl.$^5$ .................. A61K 31/435; C07F 7/02
[52] U.S. Cl. ............................ 514/317; 514/277; 546/17
[58] Field of Search .................. 546/14; 514/277

[56] References Cited

U.S. PATENT DOCUMENTS

| | | | |
|---|---|---|---|
| 4,182,767 | 1/1980 | Murai | 546/242 |
| 4,220,782 | 9/1980 | Stoltefuss et al. | 546/242 |
| 4,260,622 | 4/1981 | Junge et al. | 424/267 |
| 4,266,025 | 5/1981 | Kinast et al. | 435/84 |
| 4,278,683 | 7/1981 | Stoltefuss et al. | 424/267 |
| 4,312,872 | 1/1982 | Junge et al. | 424/267 |
| 4,405,714 | 9/1983 | Kinast et al. | 435/84 |
| 4,407,809 | 10/1983 | Junge et al. | 424/267 |
| 4,465,684 | 8/1984 | Böshagen et al. | 424/250 |
| 4,611,058 | 9/1986 | Koebernick et al. | 546/242 |
| 4,849,430 | 7/1989 | Fleet et al. | 514/315 |
| 4,871,747 | 10/1989 | Kinast et al. | 514/315 |
| 4,940,705 | 7/1990 | Böshagen et al. | 514/227.8 |
| 5,030,638 | 7/1991 | Partis et al. | 514/315 |
| 5,043,273 | 8/1991 | Scudder | 514/315 |
| 5,051,407 | 9/1991 | Böshagen et al. | 514/24 |

FOREIGN PATENT DOCUMENTS

| | | |
|---|---|---|
| 0599381 | 6/1988 | Australia . |
| 88205618 | 6/1988 | Australia . |
| 0366032 | 3/1982 | Austria . |
| 0868329 | 7/1978 | European Pat. Off. . |
| 0876020 | 5/1979 | European Pat. Off. . |
| 0282618 | 9/1988 | European Pat. Off. . |
| 0298350 | 1/1989 | European Pat. Off. . |
| 0322395 | 6/1989 | European Pat. Off. . |
| 0322643 | 7/1989 | European Pat. Off. . |
| 0328111 | 8/1989 | European Pat. Off. . |
| 0350012 | 1/1990 | European Pat. Off. . |
| 0378984 | 7/1990 | European Pat. Off. . |
| 0401194 | 12/1990 | European Pat. Off. . |
| 3024901 | 1/1982 | Fed. Rep. of Germany . |
| 3936295 | 5/1991 | Fed. Rep. of Germany . |
| 4009561 | 9/1991 | Fed. Rep. of Germany . |
| 54-106477 | 8/1979 | Japan . |
| 55-098163 | 7/1980 | Japan . |
| 55-105666 | 8/1980 | Japan . |
| 56-103163 | 8/1981 | Japan . |
| 57-144295 | 9/1982 | Japan . |
| 60-224675 | 11/1985 | Japan . |
| 62-267292 | 11/1987 | Japan . |
| 63-057550 | 3/1988 | Japan . |
| 64-38081 | 2/1989 | Japan . |
| 64-61458 | 3/1989 | Japan . |
| 2-306962 | 12/1990 | Japan . |
| 9117145 | 11/1991 | PCT Int'l Appl. . |
| 9118915 | 12/1991 | PCT Int'l Appl. . |
| 2009152 | 6/1979 | United Kingdom . |
| 2019843 | 11/1979 | United Kingdom . |
| 2067989 | 8/1981 | United Kingdom . |
| 2067990 | 8/1981 | United Kingdom . |
| 2088365 | 6/1982 | United Kingdom . |
| 9103242 | 9/1990 | World Int. Prop. O. . |

OTHER PUBLICATIONS

Hackh "Chemical Dictionary" p. 44, 1983.

Primary Examiner—Alan L. Rotman
Assistant Examiner—Celia Chang
Attorney, Agent, or Firm—Carolyn D. Moon

[57] ABSTRACT

This invention relates to novel N-derivatives of 1-deoxy nojirimycin, to the method for their preparation and to their use in the treatment of diabetes and the use against retro-viruses, particularly in the treatment of acquired immuno-deficiency syndrome (AIDS).

35 Claims, No Drawings

N-DERIVATIVES OF 1-DEOXY NOJIRIMYCIN

CROSS REFERENCE TO RELATED APPLICATIONS

This application is a continuation-in-part of U.S. Ser. No. 07/691,189 filed Apr. 25, 1991, now abandoned which is incorporated herein by reference.

FIELD OF THE INVENTION

This invention relates to novel N-derivatives of 1-deoxy nojirimycin, to the method for their preparation and to their use in the treatment of diabetes and their use against retro-viruses, particularly in the treatment of acquired immuno-deficiency syndrome (AIDS).

SUMMARY OF THE INVENTION

The present invention comprises a compound of the formula

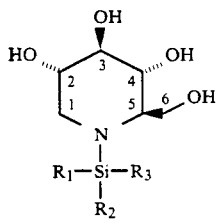

geometric isomeric forms, and the pharmaceutically acceptable salts thereof wherein Q is $C_{1-7}$ alkylene, $(CH_2)_m CH=CH(CH_2)_n$, $(CH_2)_m C\equiv C(CH_2)_n$, $(CH_2)_m CH=C=CH(CH_2)_n$, $(CH_2)_p$ phenylene, $(CH_2)_m$ cyclopentenylene, $(CH_2)_m$ cyclohexenylene, $(CH_2)_p T$, wherein T is a trivalent hydrocarbyl moiety which, together with the depicted silicon atom, form a 5- or 6-atom cyclic silicane having the partial structure of the formula

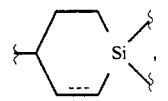

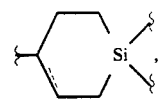

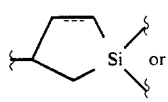

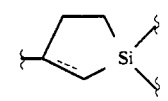

wherein the ---- (dotted line) means an optional double bond and the ∫ (wavy line) means that the moiety is connected to the rest of the molecule at that point, with m being 1, 2 or 3, n being 0, 1 or 2, p being 0, 1, 2, 3 or 4, $R_1$ is $C_{1-7}$ alkyl, $C_{1-7}$ alkoxy, $-C_{1-6}$ alkylene-$(OH)_m$, $-C_{1-6}$ alkylene-$(C_{1-6}$ alkoxy$)_m$, chloro $C_{1-6}$ alkyl, $R_2$ and $R_3$ are $C_{1-10}$ alkyl, $(CH_2)_p$-X,Y-substituted phenyl, with X and Y each being H, OH, halogen, $C_{1-6}$ alkyl, $C_{1-6}$ alkoxy, $CF_3$, CN, $NO_2$, SH or $-S-$ $C_{1-6}$ alkyl, with the proviso that when Q is $(CH_2)_p T$, then one of $R_1$, $R_2$ or $R_3$ is deleted.

The present invention also comprises methods of use for hyperglycemia, obesity associated with dietary improprieties or AIDS by administering the compound to a subject in need of such therapy.

DETAILED DESCRIPTION OF PREFERRED EMBODIMENTS

As used herein, Q is a divalent moiety bridging the 1-deoxy-nojirimycin with the silicon atom to which Q is attached. In all instances the moieties of Q are directly attached to the nitrogen atom of the 1-deoxy nojirimycin.

The $C_{1-7}$ alkylene moiety includes the straight, branched and cyclized manifestations of saturated lower aliphatic hydrocarbons including such alkylene moieties derived from alkyl radicals such as methyl, ethyl, n-propyl, isopropyl, n-butyl, cyclopropyl, pentyl, hexyl, cyclohexyl, cyclohexylmethyl, preferably n-butyl, n-propyl, methyl or ethyl, (yielding, of course such moieties as for example $(-CH_2-)$, $(-CH_2-CH_2-)$, $(-CH_2CH_2CH_2-)$, $(-CH_2-(C_6H_{10})-$ wherein the silicon is preferably attached at the meta-position of the cyclohexyl moiety, and the like). Preferably the moiety of $(CH_2)_m CH=CH(CH_2)_n$ is in its trans configuration, and preferably m is 1 and n is zero. Preferably, the $(CH_2)_m$ cyclopentenylene and cyclohexenylene moieties have their unsaturation at the carbon atom to which the silicon is attached

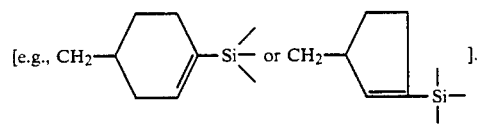

Preferably, for the $(CH_2)_p$ phenylene moiety, p is 1 or 2 and the $-SiR_1R_2R_3$ moiety is attached to the phenyl moiety at its 3-position.

Preferred $(CH_2)_p T$ moieties are illustrated as

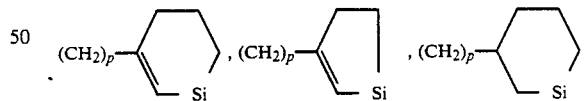

and

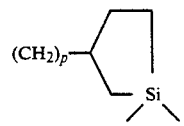

with p preferably being 1 or 2.

In those instances Wherein $R_1$ is $C_{1-7}$ alkyl or $C_{1-7}$ alkoxy, then methyl, ethyl, tert-butyl, methoxy and ethoxy are preferred. The $C_{1-7}$ alkyl of $C_{1-7}$ alkoxy can be straight chained or branched.

$C_{1-6}$ alkylene-$(OH)_m$ means an alkyl moiety having from 1 to 6 carbon atoms, at least one of the carbon atoms being substituted with one hydroxy moiety. It is preferred that m is 1, 2 or 3 representing 1, 2 or 3 hydroxy moieties being attached, preferably, to a different carbon atom of the $C_{1-6}$ alkylene—$(OH)_m$ moiety and, in such instances, it is preferred that the hydroxy be located on carbon atoms other than the carbon atom attached directly onto the silicon atom; the same concepts are also true for the mono- and polyalkoxy substituted $C_{1-6}$ alkyl moieties (—$C_{1-6}$ alkylene$_{(1-6}$ alkoxy$)_m$) in which case a methoxy moiety attached to at least one carbon atom is preferred.

Preferably the $(CH_2)_pX$,Y-substituted phenyl moieties are those wherein both X and Y are H, or one is H and the other is OH, chloro, methyl or methoxy or both are OH, Cl, methyl or methoxy. In general, in those instances wherein the Q radical contains a $(CH_2)_m$ moiety it is preferred that m be 1 or 2, and when Q contains $(CH_2)n$ moieties n preferably is zero or 1. For convenience, the

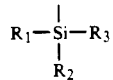

moiety and the

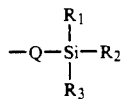

moiety of Formula I will also be referred to as —$SiR_1R_2R_3$ and —Q—Si—$R_1R_{23}$, respectively.

The pharmaceutically acceptable salts of the compounds of formula I include salts formed with non-toxic organic or inorganic acids such as, for example, from the following acids: hydrochloric, hydrobromic, sulfonic, sulfuric, phosphoric, nitric, maleic, fumaric, benzoic, ascorbic, pamoic, succinic, methanesulfonic acid, acetic, propionic, tartaric, citric, lactic, malic, mandelic, cinnamic, palmitic, itaconic and benzenesulfonic and the like.

In general the compounds of this invention are prepared by chemical reactions and procedures which are analogously known in the art and the selection of a particular route to any specific compound is governed by principles well known and appreciated by those of ordinary skill in the art.

In general the compounds of this invention may be prepared according to the reaction scheme outlined below.

Reaction Scheme A

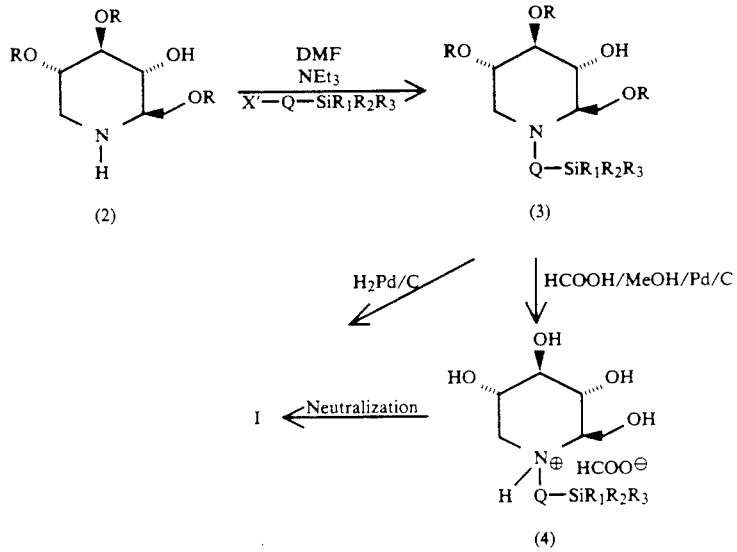

wherein Q—$SiR_1R_2R_3$ is as previously defined, R is H or Bz, Bz is benzyl, a preferred hydroxy-protecting group, X' is halogeno, mesylate or tosylate.

The synthesis of Reaction Scheme A is initiated by the condensation of an optionally hydroxy-protected 1-deoxy nojirimycin with an excess quantity (≃three times) of the appropriate X'—Q—$SiR_1R_2R_3$ reactant in the presence of an excess of triethylamine ($NEt_3$) in dimethyl formamide (DMF). Preferably X' is the iodide. The so-produced compounds (3) are purified, preferably using chromatographic techniques and are then deprotected according to standard procedures well known in the art. Preferably deprotection is effected by using transfer hydrogenation with formic acid in methanol with palladium on charcoal or by catalytic hydrogenation, preferably using palladium on charcoal in an appropriate solvent, e.g. ethanol. When transfer hydrogenation is utilized, the deprotected products (4) are in the form of quaternary salts with the $HCOO^\ominus$ anion and thus must be neutralized; the neutralization preferably being effected using an ion exchange resin such as Dowex AX-8.

In those instances wherein Q represents a bridging moiety containing an unsaturation (e.g., allylic, allenic, acetylenic, cyclopentenylene, cyclohexenylene or the unsaturated $(CH_2)_pT$ moieties) it is preferred that the 2-, 3- and 6-position hydroxy groups not be protected in view of the difficulties encountered when removing the benzyl protecting groups unless special procedures are employed (e.g., when Q contains such unsaturated moieties a process using sodium in ammonia is preferred). In those instances wherein Q is other than an unsaturated moiety, and it is preferred that the 2-, 3- and 6-positions bear a benzyl protecting group, "normal" procedures (as outlined above) may be employed for their removal. The benzyl groups may also serve as a means for obtaining the products in a more purified form. Although not required the 4-position OH group may also bear a protecting group.

It should be noted that when the above comment is made concerning the protection of the 2-, 3- and 6-OH functions, the nomenclature is that which is used in sugar chemistry using the positions of glucitol as shown in Formula I. In that instance, the OH radical of the hydroxymethyl moiety is at the 6-position, the other beta OH is at the 3-position and the two alpha OH groups are at the 2 and 4-positions. In that instance it is the 2-, 3- and 6-position hydroxy groups which would be protected prior to the condensation reaction. In the instances wherein the compounds are named as piperidine derivatives the compounds (1 and 4) would be 2($\beta$)-hydroxymethyl-1-[$R_1R_2R_3$Si-Q]-3$\alpha$,4$\beta$,5$\alpha$-piperidinetriols and thus for structures 2 and 3, the hydroxymethyl function at the 2 position, and the hydroxy functions at the 4- and 5-positions of the piperidine would be protected with a benzyl protecting group.

To illustrate the nomenclature of the compounds of this invention as piperidine derivatives the structured compound

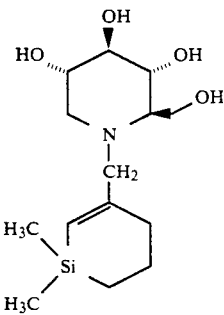

would be named [2R-(2$\beta$,3$\alpha$,4$\beta$,5$\alpha$]-2-hydroxymethyl-1-[3,3-dimethyl-3-sila-1-cyclohexenyl)methyl]-3,4,5-piperidinetriol.

1-Deoxy nojirimycin may be obtained by reducing nojirimycin (5-amino-5-deoxy-D-glucopyranose) using the method of Tetrahedron Letters, 24, 2125–2144, 1968, as referenced in European Patent Application 89 112284.8 published on Jan. 10, 1990, with publication No. 0350012. The preparation of 1-deoxy nojirimycin and its hydroxy-protected analogs (2) are also disclosed in the specific examples disclosed herein.

The X'—Q—$SiR_1R_2R_3$ reactant are either known compounds or may be prepared by methods analogously known in the art.

The following examples illustrate the preparation of the compounds of this invention.

EXAMPLE 1

Preparation of 3-(Trimethylsilyl)-1-Propanol, Methanesulfonate

Methanesulfonylchloride (0.73 ml, 9 mmol) was added dropwise to a solution of 3-(trimethylsilyl)-1-propanol (1.2 ml, 7.56 mmol) cooled at 0° C. in 20 ml of dichloromethane. After 45 minutes stirring, the reaction mixture was partitioned between water and dichloromethane, the organic phase was separated, the solvent was evaporated under reduced pressure to afford the expected 3-(trimethylsilyl)-1-propanol, methanesulfonate in crude quantitative yield.

EXAMPLE 2

Preparation of (3-Iodopropyl)Trimethysilane

An ethereal solution of magnesium iodide was prepared by adding 4.85 g (19 mmol) of iodine to 0.46 g (19 mmol) of magnesium in suspension in 40 ml of dry ether. 28 ml of this solution was added to a solution containing the crude 3-(trimethylsilyl)-1-propanol, methanesulfonate in 10 ml of ether. The reaction mixture was stirred for 3 hours at room temperature and then partitioned between ether and water, the organic phase was separated and further washed with aqueous sodium thiosulfate. After evaporation of the solvent, 1.6 g of (3-iodopropyl)trimethysilane was obtained as a colorless liquid.

EXAMPLE 3

Preparation of (3-Bromopropyl)Trimethylsilane 1.02 ml (10.9 mmol) of phosphorous tribromide in 20 ml of ether was added to a cooled (0° C., −10° C.) solution of 4 g (30.2 mmol) of 3-(trimethylsilyl)-1-propanol in 40 ml of dry ether The reaction mixture was brought back to room temperature and refluxed for 15 minutes. After bulb to bulb distillation of the crude reaction mixture 4.3g of (3-bromopropyl)trimethylsilane were isolated as a colorless liquid

EXAMPLE 4

Preparation of 4-(Trimethylsilyl)-Butanoic Acid

A solution containing 3 g (15.4 mmol) of (3-bromopropyl)trimethylsilane in 3 ml of dry ether was added to 0.375 g (15.4 mmol) of magnesium turnings in ether (40 ml final volume of solution). After 1 hour of reflux gazeous carbondioxide was bubbled through the reaction mixture (3 g, 77 mmol of dry ice). After 2 hours of stirring at room temperature the reaction mixture was partitioned between aqueous ammonium chloride and ether. The organic phase was separated, the aqueous phase was further acidified with hydrochloric acid 1N and extracted with ether. Ethereal phases were pooled and the solvent was removed under reduced pressure. Separation of the expected 4-trimethylsilylbutanoic acid from dimer of starting (3-bromopropyl)trimethylsilane was finally performed by acid base extraction. 0.62 g of 3-(trimethylsilyl)-butanoic acid was isolated as a colorless liquid.

EXAMPLE 5

Preparation of 4-(Trimethylsilyl)-1-Butanol 1.5 ml (11.4 mmol) of a 1 molar solution of borane dimethylsulfide was added to a cooled (0° C.) solution of 0.61 g (3.8 mmol) of 4-(trimethylsilyl)-butanoic acid in 20 ml of dry tetrahydrofuran. After work-up using the standard procedure (methanol, tetramethylethylene diamine) and flash chromatography purification on silica gel eluted with a 9:1 mixture of hexane and ethyl acetate, 0.4 g of 4-(trimethylsilyl)-1-butanol was obtained as a colorless liquid.

EXAMPLE 6

Preparation of 4-(Trimethylsilyl)-1-Butanol, Methanesulfonate

Starting from 0.4 g (2.53 mmol) of 4-(trimethylsilyl)-1-butanol, 0.245 ml (3.16 mmol) of methanesulfonyl chloride and 0.528 ml (4.3 mmol) of triethylamine, and using the same procedure as for the preparation of 3-(trimethylsilyl)-1-propanol, methanesulfonate, 0.5 g of the expected 4-(trimethylsilyl)-1-butanol, methanesulfonate was obtained.

EXAMPLE 7

Preparation of 4-(Iodobutyl)Trimethylsilane

Using the same procedure as described for the preparation of 3-(iodopropyl)trimethylsilane, starting from 0.5 g (2.53 mmol) of 4-(trimethylsilyl)-1-butanol methane sulfonate and 12 ml of a 0.34M ethereal solution of magnesium iodide, 0.5 g of 4-(iodobutyl)trimethylsilane was isolated as a colorless liquid.

EXAMPLE 8

Preparation of (4-Bromo-2-Butynyl)Trimethylsilane 4-(trimethylsilyl)-2-butynol [J. Pernet, B. Randrianoelina, and L. Miginiac, Tetrahedron Letters, 25, 651, (1984)] (10 g, 70 mmol) is dissolved in dry diethyl ether (150 ml) and phosphorous tribromide (2.2 ml, 23.3 mmol) is added dropwise. Then the mixture is refluxed, protected from the light during 2.5 hours. The reaction is washed twice with water, once with aqueous sodium bicarbonate and then once with water. The organic layer is dried over sodium sulfate. The solvent is evaporated under reduced pressure to afford the expected bromide (4-bromo-2-butynyl)trimethylsilane (1.4 g, 97%) which is used without purification.

EXAMPLE 9

Preparation of (4-Bromo-2-(E)Butenyl)Trimethylsilane 4-(Trimethylsilyl)-2(E)-butene-1-ol [H. Mastalerz, J. Org. Chem., 49, 4094, (1984)] (10 g, 70 mmol) is dissolved in dry diethyl ether (150 ml) and phosphorous tribromide (2.2 ml, 23.3 mmol) is added dropwise. Then the mixture is refluxed, protected from the light during 2.5 hours. The reaction is washed twice with water, once with aqueous sodium bicarbonate and then once with water. The organic layer is dried over sodium sulfate. The solvent is evaporated under reduced pressure to afford the expected bromide (4-bromo-2-(E)-butenyl)trimethylsilane (1.4 g, 97%) which is used without purification.

EXAMPLE 10

Preparation of Dimethyl(3-Iodopropyl)Phenylsilane

Dimethyl(3-chloropropyl)phenylsilane [J. W. Wilt, W. K. Chwang, C. F. Dockus and N. M. Tomiuk, J. Am. Chem. Soc., 100, 5534, (1978)] (9 g, 48.8 mmol) and sodium iodide (29.5 g, 195 mmol) are refluxed in acetone during 24 hours. The mixture is filtered and the solvent is evaporated under reduced pressure. The residue is dissolved in diethyl ether and washed with water. The organic layer is dried with sodium sulfate, filtered and concentrated under reduced pressure to afford pure dimethyl(3-iodopropyl)phenylsilane as a slightly yellow oil (12.5 g, 93%).

EXAMPLE 11

Preparation of Benzyl(Iodomethyl)Dimethylsilane

Benzyl(bromomethyl)dimethylsilane [Colm, Earborn and Foad M. S., Malmond J. Organomet. Chem., 209, 13 (1981)] (12 g, 0.05 mmol) and sodium iodide (45 g, 0.3 mmol) are refluxed with stirring in acetone (500 ml) during 24 hours. The reaction mixture is cooled, filtered and the solvent is evaporated under reduced pressure. The residue is dissolved in ether and washed with water. The organic layer is dried over sodium sulfate, filtered and concentrated under reduced pressure to afford benzyl(iodomethyl)dimethylsilane (13.7 g, 5%) as a slightly yellow oil.

EXAMPLE 12

Preparation of T-Butyl(Iodomethyl)Dimethylsilane t-Butyl(chloromethyl)dimethylsilane [Makoto Kumada, Mitsuo Ishikawa, Sajiro Meada and Katsuyata Ikura, J. Organometal. Chem. 2, 146, (1964)] (16.4 g, 0.1 mmol) and sodium iodide (60 g, 0.4 mmol) in acetone (500 ml) are refluxed with stirring during 24 hours. The reaction mixture is cooled, filtered and the solvent is evaporated under reduced pressure. The residue is dissolved in ether and washed with water. The organic layer is dried over sodium sulfate, filtered and concentrated under reduced pressure to afford t-butyl(iodomethyl)dimethylsilane (20.9 g, 80%) as a slightly yellow oil.

EXAMPLE 13

Preparation of 5-Azido-3,6-Di-O-Benzyl-5-Deoxy-D-Glucofuranose

The azide 5-azido-3,6-di-O-benzyl-5-deoxy-1,2-O-isopropylidene-α-D-glucofuranoside (U.G. Nayak and R. L. Whisler, J. Org. Chem., 33, 3582 (1968) (15.02 g, 35.3 mmol) was dissolved at 0° C. in 100 ml of a 9:1 mixture of trifluoroacetic acid and water. The mixture was stirred at 0° C. during 2 h. The trifluoroacetic acid was evaporated under reduced pressure at room temperature. The residue was taken with ether and washed with water. The organic layer was dried over sodium sulfate, filtered and concentrated under reduced pressure. Flash chromatography on silica gel and elution with a 1:1 mixture of hexane and ethyl acetate, followed by recrystallization in a mixture of hexane and ethyl acetate afforded the expected compound 5-azido-3,6-di-O-benzyl-5-deoxy-D-glucofuranose.

EXAMPLE 14

Preparation of Methyl 5-Azido-3,6-Di-O-Benzyl-5-Dioxy-D-Glucofuranoside

To a solution of 5-azido3,6-di-O-benzyl-5-deoxy-D-glucofuranose (10.23 g, 26.5 mmol) in methylene chloride (170 ml) was added methanol (11 ml) and borontrifluoroetherate (1.5 ml). The mixture was stirred 24 h at room temperature. The reaction mixture was successively washed with a saturated aqueous solution of sodium bicarbonate and then with brine. The organic layer was dried over sodium sulfate, filtered and concentrated under reduced pressure. Flash chromatography on silica gel and elution with a 1:1 mixture of hexane and ethyl acetate afforded methyl 5-azido-3,6-di-O-benzyl-5-deoxy-D-glucofuranoside as a colorless oil (9.15 g, 85%).

EXAMPLE 15

Preparation of Methyl 5-Azido-2,3,6-Tri-O-Benzyl-5-Dioxy-D-Glucofuranoside

To a suspension of sodium hydride (1.2 g, 27.5 mmol), 55% in mineral oil, washed three times with pentane) in anhydrous tetrahydrofuran (200 ml) was added quickly dropwise the alcohol methyl 5-azido-3,6-di-O-benzyl-5-deoxy-D-glucofuranoside (9.15 g, 22.9 mmol) in tetrahydrofuran (50 ml) at room temperature and under nitrogen. The mixture was stirred during 3 h at room temperature, then n-Bu₄N+I⁻ (76 mg, 0.20 mmol) was added followed by benzyl bromide (3.30 ml, 27.5 mmol) added dropwise. The mixture was stirred overnight at room temperature. After hydrolysis with saturated aqueous ammonium chloride, tetrahydrofuran was evaporated under reduced pressure. The residue was diluted with water and extracted three times with ether. The organic phase was dried over sodium sulfate. Filtration and evaporation under reduced pressure afforded an oil. Flash chromatography on silica gel and elution with a 20:80 mixture of ethyl acetate and hexane afforded the expected compound methyl 5-azido-2,3,6-tri-O-benzyl-5-deoxy-D-glucofuranoside as a colorless oil (10.88 g, 97%).

EXAMPLE 16

Preparation of 5-Azido-2,3,6-Tri-O-Benzyl-5-Deoxy-D-Glucofuranose

Methyl 5-azido-2,3,6-tri-O-benzyl-5-deoxy-D-glucofuranoside (10.8 g, 22.2 mmol) was dissolved at room temperature in tetrahydrofuran (20 ml). The solution was cooled at −10° C. and trifluoroacetic acid (120 ml) was added dropwise followed by addition of water (20 ml). The mixture was stirred at 0° C. during 24 h. The mixture was evaporated under reduced pressure without heating. The residue was taken with ether and washed with water. The organic layer was dried over sodium sulfate, filtered and concentrated under reduced pressure. Flash chromatography on silica gel and elution with a 20:80 mixture of ethyl acetate and hexane afforded 5-azido-2,3,6-tri-O-benzyl-5-deoxy-D-glucofuranose as a colorless oil (9.63 g, 90%).

EXAMPLE 17

Preparation of 5-Azido-2,3,6-Tri-O-Benzyl-5-Deoxy-D-Gluconic Acid-γ-Lactone

To a solution of the lactol 5-azido-2,3,6-tri-O-benzyl-5-deoxy-D-glucofuranose (9.36 g, 20 mmol) in acetone (240 ml) cooled to 0° C., Jones' reagent 2M (11.5 ml) was added dropwise until the color was orange. The excess of Jones' reagent was destroyed with 2-propanol (0.5 ml). The mixture was concentrated under reduced pressure. The residue was taken with water and extracted with ether. The organic phase was dried with sodium sulfate, filtered and concentrated under reduced pressure so as to afford an oil. Flash chromatography on silica gel and elution with a 1:9 mixture of ethyl acetate and hexane afforded the γ-lactone 5-azido-2,3,6-tri-O-benzyl-5-deoxy-D-gluconic acid-γ-lactone.

EXAMPLE 18

Preparation of 2,3,6-Tri-O-Benzyl-5-Deoxy-D-Gluconic Acid-δ-Lactam

To a solution of the lactone 5-azido-2,3,6-tri-O-benzyl-5-deoxy-D-gluconic acid-γ-lactone (8.16 g, 17 mmol) in ethanol (180 ml) was added lindlar catalyst (1.7 g). The mixture was hydrogenated under atmospheric pressure during 24 h. Filtration and evaporation under reduced pressure afforded an oil which was crystallized in a mixture of hexane and ether. The lactam 2,3,6-tri-O-benzyl5-deoxy-D-gluconic acid-δ-lactam was obtained as white crystals (7.4 g, 96%), m.p.: 85°–85.5° C.

EXAMPLE 19

Preparation of 2,3,6-Tri-O-Benzyl-1,5-Dideoxy-1,5-Imino-D-Glucitol

To a solution of 2,3,6-tri-O-benzyl-5-deoxy-D-gluconic acid δ-lactam (0.75 g, 1.6 mmol) in dry tetrahydrofuran (15ml) was added a 10M solution of borane in methyl sulfide (0.58 ml) under nitrogen at 0° C. The mixture was stirred 15 min at 0° C., 30 min at room temperature, then refluxed during 6 h and finally stirred overnight at room temperature. The mixture was cooled to 0° C. and the excess of borane was destroyed with methanol and stirred 1 h at room temperature. The reaction mixture was treated with gazeous hydrochloric acid and refluxed during 1 h. The solvents were evaporated under reduced pressure. The residue was dissolved in ethyl acetate and washed with a saturated aqueous solution of sodium bicarbonate. The organic layer was dried over sodium sulfate, filtered and concentrated under reduced pressure to afford an oil. Flash chromatography on silica gel and elution with ethyl acetate afforded 2,3,6-tri-O-benzyl-1,5-dideoxy-1,5-imino-D-glucitol which crystallized in methanol (0.655 g, 90%), m.p. 73°–74° C.

EXAMPLE 20

Preparation of 1,5-Dideoxy-1,5-{[4-(Trimethylsilyl)-2-Butynyl-]Imino}-D-Glucitol A solution of 1,5-dideoxy-1,5-imino-D-glucitol (also known as -deoxy-nojirimycin) (0.5 g, 3.06 mmol) and (4-bromo-2-butynyl)trimethylsilane (0.943 g, 4.6 mmol) is dissolved in dimethylformamide (15 ml) containing water (0.5 ml). Triethylamine (0.85 ml) is added. The mixture is heated at 80° C. during 24 hours. The solvent is evaporated under reduced pressure. Flash chromatography on silica gel and elution with a 8:2 mixture of chloroform and methanol affords 1,5-dideoxy-1,5-{[4-(trimethylsilyl)-2-butynyl]imino}-D-glucitol as an amorphous solid (0.24 g, 27%).

EXAMPLE 21

Preparation of 1,5-Dideoxy-1,5-{[4-(Trimethylsily)-2(Z)-Butenyl-]Imino}-D-Glucitol 1,5-Dideoxy-1,5-{[4-(trimethylsilyl)-2-butynyl-]imino}-D-glucitol (0.1 g, 0.35 mmol) is dissolved in methanol (5 ml) and lindlar catalyst (25 mg) is added. The mixture is hydrogenated at atmospheric pressure overnight. The catalyst is filtered off and the solvent is evaporated under reduced pressure to afford 1,5-dideoxy-1,5-{[4-(trimethylsilyl)-2(Z)-butenyl]imino}-D-glucitol as an amorphous solid (0.09 g, 90%).

EXAMPLE 22

Preparation of 1,5-Dideoxy-1,5-{[4-(Trimethylsily)-2(E)-Butenyl-]Imino}-D-Glucitol A solution of 1,5-dideoxy-1,5-imino-D-glucitol (0.5 g, 3.06 mmol) and (4-bromo-2-(E)butenyl)trimethylsilane (0.95 g, 4.6 mmol) in a mixture of dimethylformamide (10 ml), water (0.5 ml) and triethylamine (0.85 ml) is heated at 80° C. during 24 hours. The solvents are evaporated under reduced pressure. Flash chromatography

EXAMPLE 23

Preparation of
1,5-Dideoxy-2,3,6-Tri-O-Benzyl-1,5-{[3-(Dimethylphenylsilyl)-Propyl]Imino}-D-Glucitol A solution of 1,5-dideoxy-2,3,6-tri-O-benzyl-1,5-imino-D-glucitol (0.433 g, 1 mmol) and dimethyl(3-iodopropyl)phenylsilane (0.912 g, 3 mmol) in a mixture of dimethylformamide (6 ml) and triethylamine (0.42 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-o-benzyl-1,5-{[3-(dimethylphenylsilyl)-propyl]imino}-D-glucitol as a colorless oil (0.493 g, 81%).

EXAMPLE 24

Preparation of
1,5-Dideoxy-1,5-{[3-(Dimethylphenylsilyl)Propyl]Imino}-D-Glucitol 1,5-Dideoxy-2,3,6-tri-O-benzyl-1,5-{[3-(dimethylphenylsilyl)propyl]imino}-D-glucitol (0.45 g, 0.74 mmol) is dissolved in a 9:1 mixture of methanol and formic acid (10 ml), and palladium 10% on charcoal (0.45 g) is added. The mixture is stirred overnight at room temperature. The catalyst is removed by filtration. The solvents are evaporated under reduced pressure. The residue is dissolved in water and passed through a column of Amberlyst A26 OH⊖.

Water is evaporated under reduced pressure and flash chromatography on silica gel and elution with a 8:2 mixture of chloroform and methanol affords the expected product 1,5-dideoxy-1,5-{[3-(dimethylphenylsilyl)-propyl]imino}-D-glucitol as an amorphous solid (0.208 g, 83%). Alternatively, the titled compound may be prepared as follows: 0.4 g (2.5 mmol) of 1,5-dideoxy-1,5-imino-D-Glucitol, 1.3 g (5 mmol) of dimethyl (3-iodopropyl)phenylsilane and 0.7 ml (5 mmol) of triethylamine in 12 ml of dimethylformamide are heated at 85° C. for 40 hours. The solvents are evaporated under reduced pressure, the solid residue dissolved in 80 ml of methanol is further stirred with 7 g of dowex AG-1X8, resin is removed by filtration, solvents evaporated under reduced pressure. Flash chromotagraphy on silica gel and elution with a 95:5 to 70:30 mixture of chloroform and methanol gives rise to 0.53 g of white solid, recrystallization from ethyl acetate afford 0.45 g (60%) of expected titled compound.

EXAMPLE 25

Preparation of
1,5-Dideoxy-2,3,6-Tri-O-Benzyl-1,5-{[(Benzyldimethylsilyl)Methyl]Imino}-D-Glucitol A solution of 1,5-dideoxy-2,3,6-tri-O-benzyl-1,5-imino-D-glucitol (0.433 g, 1 mmol) and benzyl(iodomethyl)dimethylsilane (0.87 g, 3 mmol) in a mixture of dimethylformamide (6 ml) and triethylamine (0.42 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[(benzyldimethylsilyl)methyl]imino}-D-glucitol as a colorless oil (0.386 g, 65%).

EXAMPLE 26

Preparation of
1,5-Dideoxy-1,5-{[(benzyldimethylsilyl)Methyl]Imino}-D-Glucitol 1,5-Dideoxy-2,3,6-tri-O-benzyl-1,5-{[(benzyldimethylsilyl)methyl]imino}-D-glucitol (0.3 g, 0.5 mmol) is dissolved in a 9:1 mixture of methanol and formic acid (10 ml), and palladium 10% on charcoal (0.3 g) is added. The mixture is stirred overnight at room temperature. The catalyst is removed by filtration. The solvents are evaporated under reduced pressure. The residue is dissolved in water and passed through a column of Amberlyst A26 OH⊖. Water is evaporated under reduced pressure and flash chromatography on silica gel and elution with a 8:2 mixture of chloroform and methanol affords the expected product 1,5-dideoxy-1,5-{[(benzyldimethylsilyl)-methyl]-imino}-D-glucitol as an amorphous solid (0.09 g, 55%).

EXAMPLE 27

Preparation of
1,5-Dideoxy-2,3,6-Tri-O-Benzyl-1,5-{[(t-Butyldimethylsilyl)Methyl]Imino}-D-Glucitol A solution of 1,5-dideoxy-2,3,6-tri-O-benzyl-1,5-imino-D-glucitol (0.433g, 1 mmol) and t-butyl(iodomethyl)dimethylsilane (0.77 g, 3 mmol) in a mixture of dimethylformamide (6 ml) and triethylamine (0.42 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[(t-butyldimethylsilyl)-methyl]imino}-D-glucitol as a colorless oil (0.42 g, 75%).

EXAMPLE 28

Preparation of
1,5-Dideoxy-1,5-{[(t-Butyldimethylsilyl)Methyl]Imino}-D-Glucitol 1,5-Dideoxy-2,3,6-tri-O-benzyl-1,5-{[(t-butyldimethylsilyl)methyl]imino}-D-glucitol (0.4 g, 0.72 mmol) is dissolved in a 9:1 mixture of methanol and formic acid (10 ml), and palladium 10% on charcoal (0.5 g) is added. The mixture is stirred overnight at room temperature. The catalyst is removed by filtration. The solvents are evaporated under reduced pressure. The residue is dissolved in water and passed through a column of Amberlyst A26 OH⊖. Water is evaporated under reduced pressure and flash chromatography on silica gel and elution with a 8:2 mixture of chloroform and methanol affords the expected product 1,5-dideoxy-1,5-{[(t-butyldimethylsilyl)-methyl]imino}-D-glucitol as an amorphous solid (0.127 g, 61%).

EXAMPLE 29

Preparation of
1,5-Dideoxy-2,3,6-Tri-O-Benzyl-1,5-{[(Dimethyl-phenylsilyl)Methyl]Imino}-D-Glucitol A solution of 1,5-dideoxy-2,3,6-tri-O-benzyl-1,5-imino-D-glucitol (0.433 g, 1 mmol) and phenyl(iodomethyl)dimethylsilane [Chih-Tang Huang and Pao-Jen Wang, Hua Hsüeh Hsüeh Pao, 25, 341, (1959)] (0.77 g, 3 mmol) in a mixture of dimethylformamide (6 ml) and triethylamine (0.42 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[(dimethylphenylsilyl)-methyl]imino}-D-glucitol as a colorless oil (0.37 g, 64%).

EXAMPLE 30

Preparation of
1,5-Dideoxy-1,5-{[(Dimethylphenylsilyl)Methyl]Imino}-D-Glucitol 1,5-Dideoxy-2,3,6-tri-O-benzyl-1,5-{[(dimethylphenylsilyl)methyl]imino}-D-glucitol (0.35 g, 0.60 mmol) is dissolved in a 9:1 mixture of methanol and formic acid (10 ml), and palladium 10% on charcoal (0.35 g) is added. The mixture is stirred overnight at room temperature. The catalyst is removed by filtration. The solvents are evaporated under reduced pressure. The residue is dissolved in water and passed through a column of Amberlyst A26 OH$^\ominus$. Water is evaporated under reduced pressure and flash chromatography on silica gel and elution with a 8:2 mixture of chloroform and methanol affords the expected product 1,5-dideoxy-1,5-{[(dimethylphenylsilyl)-methyl]imino}-D-glucitol as an amorphous solid (0.139 g, 75%).

EXAMPLE 31

Preparation of
1,5-Dideoxy-2,3,6-Tri-O-Benzyl-1,5-{[(Trimethylsilyl)-Methyl]Imino}-D-Glucitol A solution of 1,5-dideoxy-2,3,6-tri-O-benzyl-1,5-imino-D-glucitol (0.1 g, 0.24 mmol) and (iodomethyl)-trimethylsilane (0.45 ml, 3.1 mmol) in a mixture of dimethylformamide (3 ml) and triethylamine (0.44 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[(trimethylsilyl)methyl]imino}-D-glucitol as a colorless oil (0.09 g, 75%).

EXAMPLE 32

Preparation of
1,5-Dideoxy-1,5-{[(trimethylsilyl)Methyl]Imino}-D-Glucitol 1,5-Dideoxy-2,3,6-tri-O-benzyl-1,5-{[(trimethylsilyl)-methyl]imino}-D-glucitol (0.075 g, 0.14 mmol) is dissolved in a 9:1 mixture of methanol and formic acid (12 ml), and palladium 10% on charcoal (0.3 g) is added. The mixture is stirred overnight at room temperature. The catalyst is removed by filtration. The solvents are evaporated under reduced pressure. The residue is dissolved in water and neutralized with AG1-X8, 20-50 mesh, OH$^\ominus$ form. The resin is removed by filtration, water is removed by lyophilization and the expected product 1,5-dideoxy-1,5-{[(trimethylsilyl)methyl-]imino}-D-glucitol is obtained as an amorphous solid (0.016 g, 45%).

EXAMPLE 33

Preparation of
1,5-Dideoxy-2,3,6-Tri-O-Benzyl-1,5-{[3-(Trimethylsilyl)Propyl]Imino}-D-Glucitol A solution of 1,5-dideoxy-2,3,6-tri-O-benzyl-1,5-imino-D-glucitol (0.34 g, 0.78 mmol) and (3-iodopropyl)trimethylsilane (0.57 gr, 2.34 mmol) in a mixture of dimethylformamide (5 ml) and triethylamine (0.33 ml) is heated at 80° C. during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[3-(trimethylsilyl)-propyl]imino}-D-glucitol as a colorless oil (0.405 g, 94%).

EXAMPLE 34

Preparation of
1,5-Dideoxy-1,5-{[3-(Trimethylsilyl)Propyl]Imino}-D-Glucitol 1,5-Dideoxy-2,3,6-tri-O-benzyl-1,5-{[3-(trimethylsilyl)propyl]imino}-D-glucitol (0.39 g, 0.7 mmol) is dissolved in a 9:1 mixture of methanol and formic acid (30 ml), and palladium 10% on charcoal (2 g) is added. The mixture is stirred overnight at room temperature. The catalyst is removed by filtration. The solvents are evaporated under reduced pressure. The residue is dissolved in water and neutralized with AG1-X8, 20-50 mesh, OH$^\ominus$ form. The resin is removed by filtration, water is removed by lyophilization and the expected product 1,5-dideoxy-1,5-{[3-(trimethylsilyl)-propyl]imino}-D-glucitol is obtained as an amorphous solid (0.17 g, 85%).

EXAMPLE 35

Preparation of
1,5-Dideoxy-2,3,6-Tri-O-Benzyl-1,5-{[4-(Trimethylsilyl)Butyl]-Imino}-D-Glucitol A solution of 1,5-dideoxy-2,3,6-tri-O-benzyl-1,5-imino-D-glucitol (0.043 g, 0.1 mmol) and (4-iodobutyl)-trimethylsilane (0.088 g, 0.3 mmol) in a mixture of dimethylformamide (0.8 ml) and triethylamine (0.04 ml) is stirred at room temperature during 24 hours. The solvents are evaporated under reduced pressure. The residue is dissolved in ethyl acetate, washed with water. The organic layer is dried over sodium sulfate, filtered and concentrated under reduced pressure to afford an oil. Flash chromatography on silica gel and elution with a 8:2 mixture of hexane and ethyl acetate affords the expected product 1,5-dideoxy-2,3,6-tri-O-benzyl-1,5-{[4-(trimethylsilyl)butyl]imino}-D-glucitol as a colorless oil (0.05 g, 90%).

EXAMPLE 36

Preparation of
1,5-Dideoxy-1,5-{[4-(Trimethylsily)Butyl]Imino}-D-Glucitol 1,5-Dideoxy-2,3,6-tri-O-benzyl-1,5-{[4-(trimethylsilyl)butyl]imino}-D-glucitol (0.05 g, 0.09 mmol) is dissolved in a 9:1 mixture of methanol and formic acid (15 ml), and palladium 10% on charcoal (0.2 g) is added. The mixture is stirred overnight at room temperature. The catalyst is removed by filtration. The solvents are evaporated under reduced pressure. The residue is dissolved in water and neutralized with AG1-X8, 20–50 mesh, $OH^\ominus$ form. The resin is removed by filtration, water is removed by lyophilization and the expected product 1,5-dideoxy-1,5-{[4-(trimethylsilyl)butyl]imino}-D-glucitol is obtained as an amorphous solid (0.02 g, 75%).

EXAMPLE 37

Preparation of 1,5-Dideoxy-1,5-Imino-D-Glucitol: Deoxynojirimycin 2,3,6-Tri-O-benzyl-1,5-dideoxy-1,5-imino-D-glucitol (0.2 g, 0.46 mmol) is dissolved in a 9:1 mixture of methanol and formic acid (10 ml) under an inert atmosphere and palladium 10% on charcoal (0.4 g) is added. The mixture is stirred overnight at room temperature. The catalyst is removed by filtration. The solvents are evaporated under reduced pressure. The residue is dissolved in methanol and the solution is filtered through a membrane (Millex-SR 0.5 μM). Evaporation of solvent gives a sticky solid which is further triturated in ethanol to give the expected 1,5-dideoxy-1,5-imino-D-glucitol as a beige powder (60 mg, 80%).

EXAMPLE 38

Preparation of (E)-3-Trimethylsilyl-2-Propen-1-Ol 2 g (15.6 mmol) of 3-trimethylsilyl-2-propyn-1-ol in 10 ml of dry ether are added dropwise to an ice-cooled solution of sodium bis(2-methoxyethoxy) aluminum [Red-Al. 3.4M in toluene, (7.3 ml, 25.1 mmol)] in 10 ml of dry ether. The reaction mixture is then further stirred during 2½ hours at room temperature and poured into an ice-cooled sulfuric acid (1N) ether mixture. If necessary the pH is adjusted to be slightly basic, the organic phase is then removed and the aqueous phase is further extracted with ether. The combined organic phases are dried over sodium sulfate, filtered and concentrated under reduced pressure. Rapid flash chromatography of the residue on a silica gel column eluted with a 8:2 mixture of hexane and ethyl acetate affords the expected (E)-3-trimethylsilyl-2-propen-1-ol as a colorless liquid (1.8 g, 90%).

EXAMPLE 39

Preparation of (E)-3-Trimethylsilyl-2-Propen-1-Ol, Methanesulfonate 1.6 ml (11.5 mmol) of triethylamine and 0.74 ml (9.6 mmol) of methanesulfonylchloride in 10 ml of dry dichloromethane are successively added to an ice-cooled solution of 1 g (7.6 mmol) of (E)-3-trimethylsilyl-2-propen-1-ol in 20 ml of dry dichloromethane. The reaction mixture is then further stirred during 3 hours at room temperature and poured into a water-dichloromethane mixture, the organic phase is removed, the aqueous phase is further extracted with dichloromethane. The organic phases are combined and washed with sodium bicarbonate, dried over sodium sulfate, filtered and concentrated under reduced pressure to give 1.1 g of a yellowish liquid which is further bulb to bulb distilled under reduced pressure (water pump, oven temperature 150°–200° C.) to afford 0.8 g (50%) of the expected (E)-3-trimethylsilyl-2-propen-1-ol, methanesulfonate.

EXAMPLE 40

Preparation of
1,5-Dideoxy-1,5-{[(E)-3-(Trimethylsilyl)-2-Propenyl]Imino}-D-Glucitol A solution of 1,5-dideoxy-1,5-imino-D-glucitol (0.052 g, 0.32 mmol) and (E)-3-trimethylsilyl-2-propen-1-ol, methanesulfonate (0.133 g, 0.63 mmol) in a mixture of dimethylformamide (2 ml) and triethylamine (0.09 ml, 0.63 mmol) is heated at 80° C. during 20 hours. Solvents are evaporated under reduced pressure and the residue is flash chromatographed on a silica gel column, eluted with dichloromethane: ethanol 9:1 to 7:3 to give 0.022 g (35%) of the expected 1,5-dideoxy-1,5-{[(E)-3-(trimethylsilyl)-2-propenyl]imino}-D-glucitol as a white powder.

EXAMPLE 41

Preparation of 1-Methyl-3-Trimethyl-Benzene

A mixture of 9.2 g (50 mmol) of 3-bromo-toluene and 5.84 g (50 mmol) of chlorotrimethylsilane in 100 ml of dry ether are added dropwise to 1.2 g (50 mmol) of magnesium turnings in a few milliliters of ether, some crystals of iodine are added to start the reaction. The reaction mixture is refluxed for 20 hours after the end of the addition and then poured into a saturated solution of ammonium chloride (200 ml). The aqueous solution is further extracted with ether, the ethereal extracts are combined, dried over sodium sulfate, filtered and concentrated under reduced pressure to afford 4.4 g of a yellowish liquid. Flash chromatography on a silica gel column and elution with petroleum ether give 2.3 g (30%) of the expected 1-methyl-3-trimethylsilylbenzene as a colorless liquid.

EXAMPLE 42

Preparation of
1-Bromomethyl-3-Trimethylsilyl-Benzene

A mixture of 2.5 g (15 mmol) of 1-methyl-3-trimethylsilyl-benzene and 3.1 g (16.5 mmol) of N-bromosuccinimide in 80 ml of carbon tetrachloride are refluxed in the presence of a catalytic amount of benzoyl peroxide. When succinimide has totally precipitated at the surface, the hot mixture is filtered. The filtrate is evaporated under reduced pressure, the residue obtained is dissolved in a brine-chloroform mixture. The organic phase is separated, dried over sodium sulfate, filtered and evaporated to afford 4 g of a yellowish liquid. Flash chromatography on silica gel and elution with petroleum ether give 2g (60%) of the expected 1-bromomethyl-3-trimethylsilyl-benzene as a colorless liquid.

EXAMPLE 43

Preparation of
1,5-Dideoxy-1,5-[{[3-(Trimethylsilyl)Phenyl]Methyl}Imino]-D-Glucitol A solution of 1,5-dideoxy-1,5-imino-D-glucitol (0.128 g, 0.78 mmol) and 1-bromomethyl-3-trimethylsilyl-benzene (0.3 g, 1.23 mmol) in a mixture of dimethylformamide (5 ml) and triethylamine (0.17 ml) is heated at 100° C. during 20 hours. Solvents are evaporated under reduced pressure and the residue is flash chromatographed on a silica gel column, eluted with dichloromethane:ethanol 9:1 to 7:3 to give 0.1 g (40%) of the expected 1,5-dideoxy-1,5-[{[3-(trimethylsilyl)phenyl]methyl}imino]-D-glucitol as a white powder.

EXAMPLE 44

Preparation of 1,5-Dideoxy-1,5-{[3-(Trimethylsilyl)Propyl]Imino}-D-Glucitol

Step A (3-Iodopropyl)trimethylsilane

A stirred solution of (3-chloropropyl)trimethylsilane (5.0 g, 33 mmol) and sodium iodide (7.5 g, 50 mmol) in acetone (45 ml) was heated at a reflux for 16 hours. The solution became dark yellow (iodine) with a white precipitate (NaCl). The resultant mixture was cooled to room temperature and filtered to remove the NaCl. The salt was washed with acetone (3×5 ml). The washings were combined with the filtrate and concentrated (25° C./10 Torr) leaving a two-phase mixture. The concentrate was partitioned in ethyl acetate (50 ml) and water (25 ml). The organic layer was separated, washed with aqueous sodium metabisulfite 10% (10 ml), water (20 ml), dried (MgSO4), and concentrated (250° C./10 Torr) to give 6.0 g of a pale yellow oil. This crude oil was distilled through a six-inch Vigreux column (removing some unreacted chloropropyltrimethylsilane) under water aspirator vacuum giving 4.2 g (50%) of the expected (3-iodopropyl)trimethylsilane as a colorless oil: b.p. 72° C./10 Torr.

Step B 1,5-Dideoxy-1,5-{[3-(trimethylsilyl)propyl]imino}-D-glucitol

A well stirred mixture of 1,5-dideoxy-1,5-imino-D-glucitol (0.50 g, 3.1 mmol), 3-iodopropyltrimethylsilane (1.1 g, 4.6 mmol) and sodium bicarbonate (0.38 g, 4.6 mmol) in sulfolane (5 ml) was heated at 90° C. for 3 hours and then cooled to room temperature. The mixture was diluted with water (5 ml), acidified with 1M HCl (5 ml) to pH 2–3, and allowed to stir at room temperature for 1 hour. The mixture was washed with hexane (3×5 ml) and adjusted to pH 8 with 1M sodium hydroxide (3.2 ml) precipitating the crude product. The mixture was cooled to 5° C. (ice-water bath), filtered, and the filter cake was washed with ice-water (2×3 ml) and air-dried for 1 hour to give 0.64 g of a white solid. The solid was dissolved in hot (80° C.) water (12 ml) and cooled to give 0.56 g (66%) of the desired product as white pellets.

EXAMPLE 45

Preparation of 1,5-Dideoxy-1,5-[{[2-(Trimethylsilyl)Phenyl]Methyl}Imino]-D-Glucitol A solution of 1,5-dideoxy-1,5-imino-D-glucitol formate salt (0.1 g, 0.48 mmol) and 1-bromomethyl-2-trimethylsilylbenzene [Severson et al., J. Amer. Chem. Soc. 79, 6540 (1957)] (0.23 g, 0.96 mmol) in a mixture of dimethylformamide (4 ml) and triethylamine (0.14 ml, 0.96 mmol) is heated at 90° C. overnight. Solvents are evaporated under reduced pressure and the residue is flash chromatographed on a silica gel column eluted with dichloromethane: ethanol 95:15 to 80:20 to give 0.049 (25%) of the expected 1,5-dideoxy-1,5-[{[2-(trimethylsilyl)phenyl]methyl}imino]-D-glucitol as a white solid.

EXAMPLE 46

Preparation of 1,5-Dideoxy-1,5-[{[4-(Trimethylsilyl)Phenyl]Methyl}Imino]-D-Glucitol A solution of 1,5-dideoxy-1,5-imino-D-glucitol (0.3 g, 1.8 mmol) and 1-bromomethyl-4-trimethylsilyl-benzene [Severson et al., J. Amer. Chem. Soc. 79, 6540 (1957)](0.55 g, 2.23 mmol) in a mixture of dimethylformamide (10 ml) and triethylamine (0.44 ml, 3 mmol) is heated at 70° C. during 8 hours. The solvents are evaporated under reduced pressure, the solid residue dissolved in 25 ml of methanol is further stirred with 10 g of Dowex AG-1X8, resin is removed by filtration, solvents evaporated under reduced pressure. Flash chromatography on silica gel and elution with a 95:5 to 80:20 mixture of chloroform and methanol affords 0.3 g (50%) of the expected 1,5-dideoxy 1,5-[{[4-(trimethylsilyl)phenyl]methyl}imino]-D-glucitol as a white solid.

EXAMPLE 47

Preparation of 5-Iodopentyltrimethylsilane

Step A

5-Trimethylsilyl-pentanol, methanesulfonate

As for the preparation described in Example 39, 1.4 ml (8.1 mmol) of triethylamine and 0.5 ml (6.5 mmol) of methane sulfonylchloride in 20 ml of dry dichloromethane are added to 0.87 g (5.4 mmol) of 5-trimethylsilyl-pentanol [J. Pola and V. Chvalovsky Collection Czechoslov. Chem. Commun 39, p. 2247 (1974)] to afford 1 g (78%) of the expected 5-trimethylsilyl-pentanol, methanesulfonate.

Step B (5-Iodopentyl)trimethylsilane

Following the same procedure as in Example 10, 1 g (4.2 mmol) of 5-trimethylsilyl-pentanol, methanesulfonate are reacted with 4.4 g (30 mmol) of sodium iodide in 30 ml of acetone to give raise to 0.72 g (65%) of expected (5-iodopentyl)trimethylsilane.

EXAMPLE 48

Preparation of 1,5-Dideoxy-2,3,6-Tri-O-Benzyl-1,5-{[5-(Trimethylsilyl)Pentyl]Imino}-D-Glucitol Following the same procedure as in Example 33, 0.24 g (0.55 mmol) of 1,5-dideoxy-2,3,6-Tri-O-benzyl-1,5-imino-D-glucitol in 5 ml of dimethylformamide are reacted with 0.45 g (1.66 mmol) of (5-iodopentyl)trimethylsilane and 0.23 ml (1.6 mmol) of triethylamine to afford 0.27 g (68%) of expected 1,5-dideoxy-2,3,6-Tri-O-benzyl-1,5-{[5-(trimethylsilyl)pentyl]imino}-D-glucitol as a viscous oil.

EXAMPLE 49

Preparation of 1,5-Dideoxy-1,5-{[5-(Trimethylsilyl)Pentyl]Imino}-D-Glucitol

Following the same procedure as in Example 34, 0.33 g (0.46 mmol) of 1,5-dideoxy-2,3,6-Tri-O-benzyl-1,5-{[5-trimethylsilyl)pentyl]imino}-D-glucitol in 15 ml of 9:1 mixture of methanol and formic acid, and 0.6 g of palladium 10% on charcoal give raise to.0.07 g (40%) of expected 1,5-dideoxy-1,5-{[5-(trimethylsilyl)pentyl]imino}-D-glucitol as a white solid.

EXAMPLE 50

Preparation of (6-Iodohexyl)Trimethylsilane

Step A

6-Trimethylsilyl-hexanol, methanesulfonate

As for the preparation described in Example 39, 0.32 ml (2.5 mmol) of triethylamine and 0.3 ml (2.2 mmol) of methanesulfonylchloride in 5 ml of dry dichloromethane are added to 0.29 g (1.8 mmol) of 6-trimethylsilyl hexanol [J. Pola and V. Chvalovsky Collection Czechoslov. Chem. Commun 39, p. 2247 (1974)] to afford 0.3 g (70%) of the expected 6-trimethylsilyl-hexanol, methanesulfonate.

Step B (6-Iodohexyl)trimethylsilane

Following the same procedure as in Example 10, 0.3 g (1.2 mmol) of 6-trimethylsilyl-hexanol, methanesulfonate are reacted with 1 g (7.2 mmol) of sodium iodide in 15 ml of acetone to give raise to 0.23 g (68%) of expected (6-iodohexyl)trimethylsilane.

EXAMPLE 51

Preparation of 1,5-Dideoxy-2,3,6-Tri-O-Benzyl-1,5-{[6-(Trimethylsilyl)Hexyl]Imino}-D-Glucitol Following the same procedure as in Example 33, 0.23 g (0.54 mmol) of 1,5-dideoxy-2,3,6-Tri-O-benzyl-1,5-imino-D-glucitol in 5 ml of dimethylformamide ar reacted with 0.23 g (0.8 mmol) of (6-iodohexyl)trimethylsilane and 0.11 ml (0.8 mmol) of triethylamine to afford 0.15 g (45%) of expected 1,5-dideoxy-2,3,6-Tri-O-benzyl-1,5-{[6-(trimethylsilyl)hexyl]imino}-D-glucitol as a viscous oil.

EXAMPLE 52

Preparation of 1,5-Dideoxy-1,5-{[6-(Trimethylsilyl)Hexyl]Imino}-D-Glucitol 0.18 g (0.3 mmol) of 1,5-dideoxy-2,3,6-Tri-O-benzyl-1,5-{[6-(trimethylsilyl)hexyl]imino}-D-glucitol 20 ml of a 4:1 mixture of ethanol and water and 0.1N hydrochloric acid (3 ml, 0.3 mmol) are hydrogenated at atmospheric pressure in presence of 60 mg of palladium 10% on charcoal to afford 0.065 g (66%) of expected 1,5-dideoxy-1,5-{5-(trimethylsilyl)hexyl]imino}-D-glucitol as a white solid.

EXAMPLE 53

Preparation of 1,5-Dideoxy-1,5-{[4-(Dimethylphenylsilyl)Butyl]Imino}-D-Glucitol

Step A

Preparation of dimethyl-(4-iodobutyl)-phenylsilane

Following the same procedure as in Example 44 Step A, 5 g (19 mmol) of dimethyl-(4-chlorobutyl)-phenylsilane in 50 ml of acetone are refluxed for 60 hours with 17 g (114 mmol) of sodium iodide to afford 5.6 g (83%) of expected dimethyl-(4-iodobutyl)-phenylsilane.

Step B

Preparation of 1,5-dideoxy-1,5-{[4-(dimethylphenylsilyl)butyl]imino}-D-glucitol

A well stirred mixture of 0.5 g (3 mmol) of 1,5-dideoxy-1,5-imino-D-glucitol, 1.78 g (5 mmol) of dimethyl-(4-iodobutyl)-phenylsilane and 0.7 ml (3 mmol) of triethylamine in 12 ml of dimethylformamide and 1 ml of water was heated at 80° C. overnight. The solvents are evaporated under reduced pressure and the residue is flash chromatographed on silica gel column, eluted with chloroform: methanol 95:5 to 70:30 to afford after methanol-water cristallization of the chromatographed compound 0.2 g (20%) of expected 1,5-dideoxy-1,5-{[4-(dimethylphenylsilyl)butyl]imino}-D-glucitol as white crystals.

EXAMPLE 54

Preparation of 1,5-Dideoxy-1,5-{[(Z)-3-(Trimethylsilyl)-2-Propenyl]Imino}-D-Glucitol

Step A (Z)-3-Trimethylsilyl-2-propen-1-ol, methanesulfonate

As for the preparation described in Example 39, 0.95 ml (6.8 mmol) of triethylamine and 0.44 ml (5.6 mmol) of methanesulfonylchloride in 5 ml of dry dichloromethane are added to 0.59 g (4.5 mmol) of (Z)-3-trimethylsilyl-2-propen-1-ol [Paquette et al., J. Org. Chem. 54 (18), 4278 (1989] to afford after bulb to bulb distillation (150° C., 20 mm Hg 0.6 g (64%) of expected (Z)-3-trimethylsilyl-2-propen-1-ol, methanesulfate contaminated by 8 to 10% of the (E) isomer.

Step B 1,5-Dideoxy-1,5-{[(Z)-3-(trimethylsilyl)-2-propenyl]imino}-D-glucitol Following the same procedure as in Example 40, 0.24 g (1.4 mmol) of 1,5-dideoxy-1,5-imino-D-glucitol, 0.65 g (2.6 mmol) of (Z)-3-trimethylsilyl-2-propen-1-ol, methane-sulfonate and 0.19 ml (1.4 mmol) of triethylamine in 10 ml of dimethylformamide are heated at 80° C. overnight. Solvents are removed under reduced pressure and the residue is flash chromatographed on a silica gel column eluted with dichloromethane: methanol 98:2 to 85:15 to give after methanol-water cristallization 0.13 g (30%) of expected 1,5-dideoxy-1,5-{[(Z)-3-(trimethylsilyl)-2-propenyl]imino}-D-glucitol as white crystals.

EXAMPLE 55

Preparation of 1,5-Dideoxy-1,5-{[(E)-3-(T-Butyldimethylsilyl)-2-Propenyl]Imino}-D-Glucitol

Step A (E)-3-(t-butyldimethylsilyl)-2-propen-1-ol-methanesulfonate

As for the preparation described in Example 39, 1.6 ml (11.4 mmol) of triethylamine and 0.74 ml (9.55 mmol) of methanesulfonylchloride in 15 ml of dry dichloromethane are added to 1.3 g (7.6 mmol) of (E)-3-(t-butyldimethylsilyl)-2-propen-1-ol. [Lipshutz et al., J. Org. Chem. 54(21), 4975 (1989)] in 20 ml of dry dichloromethane to give after purification by flash chromatography on silica gel and elution with petroleum ether: ethyl acetate 9:1 1.3 g (67%) of expected (E)-3-(t-butyldimethylsilyl)-2-propen-1-ol, methanesulfonate as a colorless liquid.

1,5-Dideoxy-1,5-{[(E)-3-(t-butyldimethylsilyl)-2-propenyl]imino}-d-glucitol

Following the same procedure as in Example 40, 0.3 g (1.85 mmol) of 1, 5-dideoxy-1,5-imino-D-glucitol, 0.65 g (2.6 mmol) of (E)-3-(t-butyldimethylsilyl)-2-propen-1-ol, methanesulfonate and 0.48 ml (3.4 mmol) of triethylamine in 13 ml of dimethylformamide are heated at 80° C. overnight. Solvents are removed under reduced pressure and the residue is flash chromatographed on a silica gel column eluted with dichloromethane-methanol 100:0 to 90:10 to give after methanol-water recristallization 0.15 g (35%) of expected {[(E)-3-(t-butyldimethylsilyl)-2-propenyl]imino}-D-glucitol as white crystals.

EXAMPLE 56

Preparation of
1,5-Dideoxy-1,5-{[(E)-3-(Phenyldimethylsilyl)-2-Propenyl]Imino}-D-Glucitol

Step A (E)-3-(Phenyldimethylsilyl)-2-propen-1-ol, methanesulfonate

As for the preparation described in Example 39, 1.5 ml (10 mmol) of triethylamine and 0.75 ml (10 mmol) of methanesulfonylchloride in 30 ml of dry dichloromethane are added to 1.55 g (8 mmol) of (E)-3-(phenyldimethylsilyl)-2-propen-1-ol. [Miura et al., Bull. Chem. Soc. Jpn, 63(6), 1665 (1990)] in 25 ml of dry dichloromethane to give after purification by flash chromatography on silica gel and elution with a 9:1 petroleum ether:ethylacetate mixture 1.2 g (45%) of expected (E)-3-(phenyldimethylsilyl)-2-propen-1-ol, methansulfonate as a colorless liquid.

Step B 1,5-Dideoxy-1,5-{[(E)-3-(phenyldimethylsilyl)-2-propenyl]imino}-D-glucitol Following the same procedure as in Example 40, 0.3 g (1.8 mmol) of 1,5-dideoxy-1,5-imino-D-glucitol, 0.96 g (3.5 mmol) of (E)-3-(phenyldimethylsilyl)-2-propen-1-ol, methanesulfonate and 0.25 ml (1.8 mmol) of triethylamine in 20 ml of dimethylformamide are heated at 80° C. overnight. Solvents are removed under reduced pressure and the residue is flash chromatographed on a silica gel column eluted with dichloromethane-methanol 100:0 to 90:10 to give after methanol-water recrystallization 0.16 g (23%) of expected 1,5-dideoxy-1,5-{[(E)-3-(phenyldimethylsilyl)-2-propenyl]imino}-D-glucitol as white crystals.

EXAMPLE 57

Preparation of
(Z)-O-(T-Butyldimethylsilyl)-3-(T-Butyldimethylsilyl)-2-Propen-1-Ol

Step A

Preparation of O-(t-butyldimethylsilyl)-3-(t-butyldimethylsilyl)-2-propyn-1-ol 140 ml of butyllithium (15% solution in hexane, 1.6M, 0.22 mol) in 100 ml of dry tetrahydrofuran is added dropwise to a cooled (−78° C.) solution of 5.6 g (0.1 mol) of propargyl alcohol in 100 ml of dry tetrahydrofuran. After 2 hours stirring at −78° C., 33 g (0.219 mol) of t-butyldimethylchlorosilane in 100 ml of dry tetrahydrofuran is added dropwise to the reaction mixture.

Stirring is maintained overnight while temperature slowly raised to room temperature. The reaction mixture is filtered and the filtrate is concentrated under reduced pressure. The residue is partitioned between diethyl ether and water. The organic phase is removed and the aqueous is further extracted with ether. The combined organic are dried over sodium sulfate, filtered and concentrated under reduced pressure to afford 27 g (0.095 mmol) (95% crude yield) of expected O-(t-butyldimethylsilyl)-3-(t-butyldimethylsilyl)-2-propyn-1-ol as a orange solid.

Step B

Preparation of (Z)-0-(t-butyldimethylsilyl)-3-(t-butyldimethylsilyl)-2-propen-1-ol An ethanol solution of Nickel-P$_2$ catalyst (1 mmol) prepared from 248 mg of nickelous acetate tetrahydrate in 10 ml ethanol and 38 mg, (1 mmol) of sodium borohydride in 1 ml of ethanol. [Brown et al., J. C.S. Chem. Comm. 553 (1973)] is put under hydrogen atmosphere (hydrogenation apparatus). 0.134 ml (2 mmol) of freshly distilled ethylene diamine and 2.8 g (10 mmol) of O-(t-butyldimethylsilyl)-3-(t-butyldimethylsilyl)-2-propyn-1-ol in 60 ml ethanol were successively added to the solution. Reaction mixture is stirred at room temperature for 48 hours. Catalyst is removed by filtration through celite. Most of the solvent is removed by evaporation and the residue is dissolved in an ether-water mixture, aqueous is further extracted with ether, organic are dried with sodium sulfate, filtered and concentrated under reduced pressure. Flash chromatography on silica gel and elution with petroleum ether afford 1.4 g (50%) of the expected (Z)-O-(t-butyldimethylsilyl)-3-(t-(butyldimethylsilyl)-2-propen-1-ol as a colorless liquid.

EXAMPLE 58

Preparation of
(Z)-3-(T-Butyldimethylsilyl)-2-Propen-1-Ol

A mixture of 1.2 g, 4.2 mmol) of (Z)-O-(t-butyldimethylsilyl)-3-(t-butyldimethylsilyl)-2-propen-1-ol and 0.04 g of diisocyanate tetrabutylstannoxane [Otera, Nozaki, Tetrahedron Lett., 27, 5743 (1986)] in 140 ml of methanol is refluxed for 9 hours. Most of solvent is removed under reduced pressure and the residue is dissolved in a ether-water mixture. Etheral phase is washed with water and brine ,dried with sodium sulfate, filtered and concentrated under reduced pressure to afford 0.7 g (quantitatif crude yield) of (Z)-3-(t-butyldimethylsilyl)-2-propen-1-ol as a colorless liquid.

EXAMPLE 59

Preparation of
1,5-Dideoxy-1,5-{[(Z)-3-(T-Butyldimethylsilyl)-2-Propenyl]Imino-}-D-Glucitol

Step A

[(Z)-3-(T-Butyldimethylsilyl)-2-propen-1-ol-methanesulfonate

As for the preparation described in Example 39, 0.9 ml (6.4 mmol) of triethylamine and 0.42 ml (5.4 mmol) of methanesulfonylchloride in 5 ml of dry dichloromethane are added to 0.75 g (4.3 mmol) of (Z)-3-(t-butyldimethylsilyl)-2-propen-1-ol in 5 ml dichloromethane to give after purification by flash chromatographed on silica gel and elution with petroleum ether-ethyl acetate 10:0 to 9:1 0.63 g (60%) of expected (Z)-3-(t-butyldimethylsilyl)-2-propen-1-ol-methanesulfonate as a colorless liquid.

Step B 1,5-Dideoxy-1,5-{(Z)-3-(t-butyldimethylsilyl)-2-propenyl]imino-}-D-glucitol Following the same procedure as in Example 40, 0.24 g (1.47 mmol) of 1,5-dideoxy-1,5-imino-D-glucitol, 0.65 g (2.6 mmol) of (Z)-3-(t-butyldimethylsilyl)-2-propen-1-ol-methanesulfonate and 0.2 ml (1.4 mmol) of triethylamine in 10 mmol of dimethylformamide are heated at 80° C. overnight. Solvents are removed under reduced pressure and the residue is flash chromatographed on a silica gel column eluted with dichloromethane: methanol 98:2 to 85:15 to give after methanol-water recrystallization 0.15 g (25%) of expected 1,5-dideoxy-1,5-{[(Z)-3-(t-butyldimethylsilyl)-2-propenyl]imino-}-D-glucitol as white crystals.

EXAMPLE 60

Preparation of
1,5-Dideoxy-1,5-{[(Ethyldimethylsilyl)-Methyl-]Imino}-D-Glucitol

Step A

Preparation of iodomethyldimethylvinylsilane

Following the same procedure as in Example 10, 5 g (37 mmol) of chloromethyldimethylvinylsilane are reacted with 22 g (146 mmol) of sodium iodide in 100 ml of acetone to give 7 g (83%) of expected iodomethyldimethylvinylsilane.

Step B

Preparation of 1,5-dideoxy-2,3,6-tri-O-benzyl-1,5-{[vinyldimethylsilyl)methyl]imino}-D-Glucitol Following the same procedure as in Example 31, 0.123 g (0.28 mmol) of 1,5-dideoxy-2,3,6-tri-O-benzyl-1,5-imino-D-Glucitol in 3 ml of dimethylformamide are reacted with 0.24 g (0.85 mmol) of iodomethyldimethylvinylsilane and 0.2 ml (1.4 mmol) of triethylamine to afford 0.122 g (80%) of the expected 1,5-dideoxy-2,3,6-tri-O-benzyl-1,5-{[vinyldimethylsilyl)methyl]imino}-D-Glucitol.

Step C

Preparation of 1,5-dideoxy-1,5-{[(ethyldimethylsilyl)-methyl]imino}-D-glucitol

Following the same procedure as in Example 34, 0.12 g (0.2 mmol) of 1,5-dideoxy-2,3,6-tri-O-benzyl-1,5-{[vinyldimethylsilyl)methyl]imino}-D-Glucitol in 10 cc of 9:1 mixture of methanol and formic acid and 0.3 g of palladium 10% on charcoal gave rise after pentane trituration to 0.048 g (80%) of the expected 1,5-dideoxy-1,5-{[(ethyldimethylsilyl)-methyl]imino}-D-glucitol as a white solid.

EXAMPLE 61

Preparation of
1,5-Dideoxy-1,5-{[Propyldimethylsilyl)-Methyl-]Imino}-D-Glucitol

Step A

Preparation of (chloromethyl)allyldimethylsilane

To an etheral solution of allylmagnesiumbromide freshly prepared starting from 16 g (0.13 mol) of allylbromide and 3.17 g (0.13 mol) of magnesium turnings in 140 ml of dry ether was added 9.9 g of chloromethyldimethylchlorosilane in 130 ml of dry ether, the reaction mixture is refluxed overnight and then poured into 400 ml of an ice cooled saturated ammonium chloride solution. Organic phase is separated, aqueous is further extracted with ether, organic are combined, washed with brine, dried over sodium sulfate and filtered. Solvent is removed under reduced pressure to afford 7.5 g (40%) of expected (chloromethyl)allyldimethylsilane.

Step B

Preparation of (iodomethyl)allyldimethylsilane

Following the same procedure as reported in Example 10, 3 g (0.02 mol) of (chloromethyl)allyldimethylsilane are reacted with 12 g (0.08 mol) of sodium iodide in 60 ml of acetone to give 3.8 g (80%) of expected (iodomethyl)allyldimethylsilane as a yellowish liquid.

Step C

Preparation of 1,5-dideoxy-2,3,6-Tri-O-Benzyl-1,5-{[(allyldimethylsilane)methyl]imino}-D-Glucitol Following the same procedure as in Example 31, 0.355 g (0.82 mmol) of 1,5-dideoxy-2,3,6-tri-O-benzyl-1,5-imino-D-glucitol in 10 ml of dimethylformamide are reacted with 0.49 g (2.1 mmol) of iodomethylallyldimethylsilane and 0.29 ml (2 mmol) of triethylamine to afford, after flash chromotagraphy on silical gel, 0.12 g (30%) of expected compound as a viscous oil.

Step D

Preparation of 1,5-dideoxy-1,5-{[propyldimethylsilyl)-methyl]imino}-D-Glucitol

Following the same procedure as in Example 34, 0.1 g (0.2 mmol) of 1,5-dideoxy-2,3,6-Tri-O-Benzyl-1,5-[[(allyldimethylsilyl)methyl]imino]-D-Glucitol in 20 ml of 9:1 mixture of methanol and formic acid and 0.2 g of palladium 10% on charcoal gave rise after flash chromatography on silica gel and elution with a 9:1 to 8:2 mixture of chloroform and methanol 0.025 g (40%) to expected 1,5-dideoxy-1,5-{[propyldimethylsilyl)-methyl]imino}-D-Glucitol as a white powder.

Enzymes which catalyze the hydrolysis of complex carbohydrates, e.g. α-glycosidases, convert non-absorbable carbohydrates into absorbable sugars. The rapid action of these enzymes, particularly following the intake of high levels of carbohydrates, lead to acute high levels in blood glucose which, in the case of diabetics, lead to undesirable manifestations, thus it has been a long-sought goal to find compounds which will obviate the hyperglycemia caused by dietary improprieties. Similarly, in the case of obesity the control of high levels of blood glucose, with its subsequent conversion to fat, caused by the catalysis of carbohydrates has inspired the quest for compounds which will obviate the problems associated with dietary improprieties. "Dietary improprieties" means eating habits associated with overeating, overdrinking, and failure to maintain a balanced diet such as the excessive intake of carbohydrates, which metabolize to glucose and which lead to obesity.

The compound of the present invention are administered to subjects in need of such therapy, e.g., mammals such as humans. The compounds of this invention (I) are potent and long-lasting inhibitors of α-glycosidase and, by standard laboratory methods for determining serum glucose levels, are shown to be useful for the treatment of disease states caused by the underutilization and/or overproduction of serum glucose without adversely affecting the rate of transport across cell membranes. Thus, the compounds are useful in the treatment of diabetes and obesity.

In the practice of this invention, an effective amount of a compound of this invention is that amount required to reduce the amount of serum glucose (relative to a control) following the ingestion of carbohydrates convertible to absorbable glucose. The specific dosage for the treatment of any specific patient suffering from either disease state will depend upon such factors as size, type and age of the patient as well as the patients' dietary habits and the severity of the disease state, all of which are factors normally familiar to and considered by the attending diagnostician treating the patient. Generally, the compounds are to be administered orally at a dose of 0.01 to 2 milligrams per kilogram of body weight (MPK) with a dose of 0.025 to 0.5 MPK being preferred. The compounds preferably are to be administered orally at mealtimes in single or multiple unit doses containing 1 mg to 10 mg. Of course, in the treatment of obesity, the term includes the practice of treating the disease as well as continued administration of dose regimens suitable for the maintenance of the desired weight for the patient.

It is also to be found that the compounds of the instant invention (I) will exert an inhibitory effect on glycosidase enzymes that are essential for elaboration of the final structure of the oligosaccharide side-chains of glycoproteins, particularly the HIV (gp 120) glycoprotein. Suitable assay techniques, e.g. syncytial formation, the reverse transcriptase assay, immunofluorescence tests and electron microscopy, may be used to evaluate the effects on HIV viral growth and for determining dose regimens. Anti-viral effects may be confirmed by immunofluorescence with serum for virally infected patients. In the treatment of the HIV related disease states (e.g., AIDS), as well as other retroviral glycoprotein related disease states, unlike the treatment of diabetes and obesity, the compounds of this invention may be administered by parenteral means; specific doses being within the above stated dose range for treatment of diabetes and obesity. In addition to treating AIDS with the compounds of this invention, the compounds of this invention may also be effectively utilized in conjunctive therapy with compounds known to be useful in treating patients with AIDS such as for example 2,3-dideoxycytidine, 2,3-dideoxyadenine, interferon, interleukin-2 and the like.

In practising the end-use application of the compounds of this invention, the compounds are preferably incorporated in a pharmaceutical formulation comprising a pharmaceutical carrier in admixture with a compound of this invention. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups emulsions, dispersions and wettable and effervescent powders, and can contain suitable excipients known to be useful in the preparation of the particular type of composition desired Suitable pharmaceutical carriers and formulation techniques are found in standard texts, such as Remington's Pharmaceutical Sciences, Mack Publishing Company, Easton, Pa., incorporated herein by reference.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934 and 4,031,894, incorporated herein by reference. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the receipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636, incorporated herein by reference. At least two types of occurs when the matrix is non-porous. The pharmaceutically effective compound dissolves in and diffuses through the matrix itself. Release by microporous flow occurs when the pharmaceutically effective compound is transported through a liquid phase in the pores of the matrix.

As is true for most classes of therapeutic agents certain subgeneric groups and certain specific compounds are preferred. For the compounds embraced within this application the preferred sub-generic groups are those wherein Q is $C_{1-7}$ alkylene, $(CH_2)_m CH=CH(CH_2)_n$, $(CH_2)_p$ phenylene, $(CH_2)_m$ cyclopentenylene, $(CH_2)_m$ cyclohexenylene or $(CH_2)_p T$ moieties. Preferred $R_1$ moieties are $C_{1-7}$ alkyl, phenyl or a hydroxylated alkyl, and preferred $R_2$ and $R_3$ moieties are $C_{1-10}$ alkyl, phenyl or benzyl.

The following compounds of Formula 5 illustrate the preferred specific compounds:

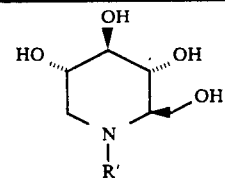

(5)

| R' |
| --- |
| $-CH_2-Si(CH_3)_3$ |
| $-(CH_2)_3-Si(CH_3)_3$ |
| $-(CH_2)_4-Si(CH_3)_3$ |
| $-CH_2-Si(CH_3)_2 C_6H_5$ |
| $-CH_2-Si(CH_3)_2 C_2H_5$ |
| $-CH_2-Si(CH_3)_2 C_3H_7$ |
| $-CH_2-CH=CH-Si(CH_3)_3$ (trans) |

-continued

| 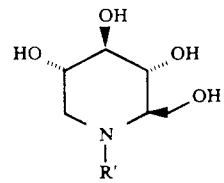 (5) |
|---|
| R' |
| 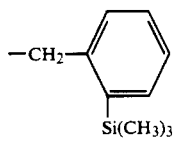 |
| 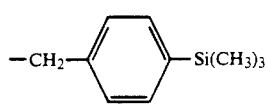 |
| 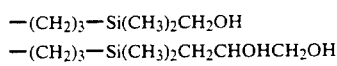 |
| 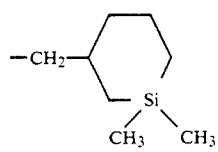 |
| 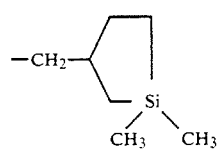 |
| 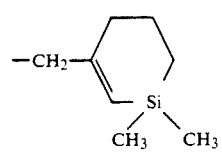 |
| 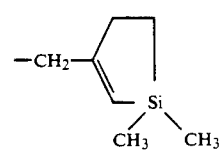 |
| 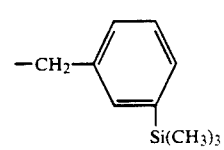 |

What is claimed is:

1. A compound of the formula

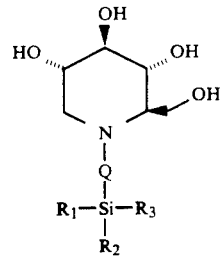

geometric isomeric forms, and the pharmaceutically acceptable salts thereof wherein Q is $C_{1-7}$ alkylene, $(CH_2)_m CH=CH(CH_2)_n$, $(CH_2)_m C\equiv C(CH_2)_n$, $(CH_2)_m(CH=C=CH(CH_2)_n$, $(CH_2)_p$ phenylene, $(CH_2)_m$ cyclopentenylene, $(CH_2)_m$ cyclohexenylene, $(CH_2)_p T$, where T is a trivalent hydrocarbyl moiety which, together with the depicted silicon atom, forms a 5- or 6-atom cyclic silicane having the partial structure of the formula

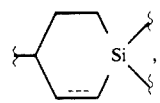

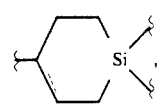

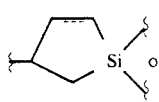 or

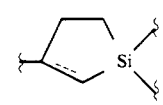

wherein the ---- (dotted line) means an optional double bond with m being 1, 2 and 3, n being 0, 1 or 2, p being 0, 1, 2, 3 or 4, $R_1$ is $C_{1-7}$ alkyl, $C_{1-7}$ alkoxy, —$C_{1-6}$ alkylene—$(OH)_m$, —$C_{1-6}$ alkylene—$(C_{1-6}$ alkoxy$)_m$, chloro $C_{1-6}$ alkyl, $R_2$ and $R_3$ are $C_{1-10}$ alkyl, $(CH_2)_p$—X,Y-substituted phenyl with X and Y each being H, OH, halogen, $C_{1-6}$ alkyl, $C_{1-6}$ alkoxy, $CF_3$, CN, $NO_2$, SH or —S— $C_{1-6}$ alkyl, with the proviso that when Q is $(CH_2)_p T$, then one of $R_1$, $R_2$ or $R_3$ is deleted.

2. The compound of claim 1 wherein Q is a $C_{1-7}$ alkylene.

3. The compound of claim 2 wherein $R_1$, $R_2$ and $R_3$ are $C_{1-7}$ alkyl.

4. The compound of claim 2 wherein the $C_{1-7}$ alkyl is methyl.

5. The compound of claim 2 wherein $R_1$ is a hydroxylated $C_{1-6}$ alkyl.

6. The compound of claim 1 wherein Q is $(CH_2)_m HC=CH(CH_2)_n$.

7. The compound of claim 6 wherein $R_1 R_2$ and $R_3$ are $C_{1-7}$ lower alkyl.

8. The compound of claim 1 wherein Q is $(CH_2)_p T$.

9. The compound of claim 8 wherein $R_1$ and $R_2$ are $C_{1-7}$ alkyl and $R_3$ is deleted.

10. The compound of claim 9 wherein the cyclic silicane of $(CH_2)_pT$ is unsaturated.

11. The compound of claim 1 wherein Q is $-CH_2$-phenylene and $R_1$, $R_2$ and $R_3$ are each $C_{1-7}$ alkyl.

12. The compound of claim 1 wherein $-Q-Si-R_1R_2R_3$ is $-CH_2-Si-(CH_3)_3$.

13. The compound of claim 1 wherein $-Q-Si-R_1R_2R_3$ is $-(CH_2)_3-Si(CH_3)_3$.

14. The compound of claim 1 wherein $-Q-Si-R_1R_2R_3$ is $-(CH_2)_4-Si(CH_3)_3$.

15. The compound of claim 1 wherein $-Q-Si-R_1R_2R_3$ is $-CH_2Si(CH_3)_2C_6H_5$.

16. The compound of claim 1 wherein $-Q-Si-R_1R_2R_3$ is $-CH_2Si(CH_3)_2C_2H_5$.

17. The compound of claim 1 wherein $-Q-Si-R_1R_2R_3$ is $-CH_2Si(CH_3)_2C_3H_7$.

18. The compound of claim 1 wherein $-Q-Si-R_1R_2R_3$ is trans-$CH_2-CH=CH-Si(CH_3)_3$.

19. The compound of claim 1 wherein $-Q-Si-R_1R_2R_3$ is cis—$CH_2-(CH=CH-Si(CH_3)_3$.

20. The compound of claim 1 wherein $-Q-Si-R_1R_2R_3$ is $-(CH_2)_3-Si(CH_3)_2CH_2OH$.

21. The compound of claim 1 wherein $-Q-Si-R_1R_2R_3$ is $-(CH_2)_3-Si(CH_3)_2CH_2CHOHCH_2OH$.

22. The compound of claim 1 wherein $-Q-Si-R_1R_2R_3$ is

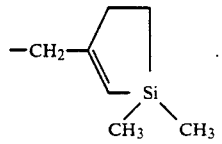

23. The compound of claim 1 wherein $-Q-Si-R_1R_2R_3$ is

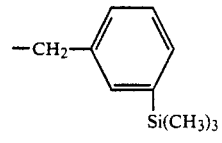

24. The compound of claim 1 wherein $-Q-Si-R_1R_2R_3$ is

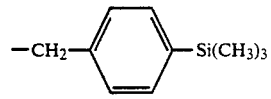

25. The compound of claim 1 wherein $-Q-Si-R_1R_2R_3$ is

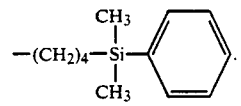

26. The compound of claim 1 wherein $-Q-Si-R_1R_2R_3$ is

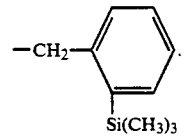

27. The compound of claim 1 wherein $-Q-Si-R_1R_2R_3$ is $-(CH_2)_5-Si(CH_3)_3$.

28. The compound of claim 1 wherein $-Q-Si-R_1R_2R_3$ is $-(CH_2)_6-Si(CH_3)_3$.

29. The compound of claim 1 wherein $-Q-Si-R_1R_2R_3$ is the cis form of $-CH_2-CH=CH-Si(CH_3)_2-C(CH_3)_3$.

30. The compound of claim 1 wherein $-Q-Si-R_1R_2R_3$ is the trans form of $-CH_2-CH=CH-Si(CH_3)_2-C(CH_3)_3$.

31. The compound of claim 1 wherein $-Q-Si-R_1R_2R_3$ is

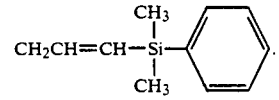

32. The compound of claim 31 in the trans form.

33. The compound of claim 1 wherein $-Q-Si-R_1R_2R_3$ is

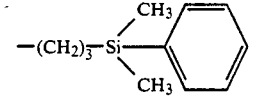

34. A method for treatment of hyperglycemia which comprises administering a therapeutically effective amount of a compound of claim 1 to a subject in need of such therapy.

35. The compound of claim 1 in combination with a pharmaceutically acceptable carrier.

* * * * *

UNITED STATES PATENT AND TRADEMARK OFFICE
CERTIFICATE OF CORRECTION

PATENT NO. : 5,252,587
DATED : October 12, 1993
INVENTOR(S) : Brigitte Lesur, Jean-Bernard Ducep, Charles Danzin It is certified that error appears in the above-identified patent and that said Letters Patent is hereby corrected as shown below:

At Column 1, line 26, the patent reads "N" and should read "N".

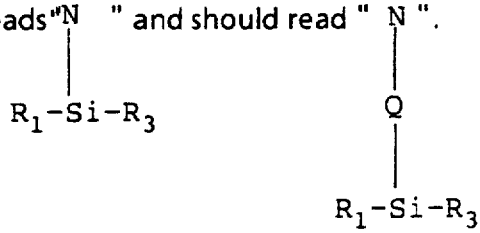

At column 3, line 11, the patent reads "$(_{1-6}$" and should read "$(C_{1-6}$". At column 3, line 61, the patent reads "$R_{23}$" and should read "$R_2R_3$". At column 8, line 8, the patent reads "T-Butyl" and should read "t-Butyl". At column 8, line 44, the patent reads "-Dioxy-" and should read "-Deoxy-". At column 8, line 45, the patent reads "azido3" and should read "azido-3". At column 8, line 61, the patent reads "-Dioxy-" and should read "-Deoxy-". At column 10, line 34, the patent reads "-deoxy" and should read "1-deoxy". At column 10, line 47, the patent reads "(Trimethylsily)" and should read "(Trimethylsilyl)". At column 10, line 60, the patent reads "(Trimethylsily)" and should read "(Trimethylsilyl)". At column 19, line 1, the patent reads ".0.07" and should read "0.07". At column 19, line 35, the patent reads "ar" and should read "are". At column 19, line 48, the patent reads "glucitol 20 ml" and should read "glucitol dissolved in 20 ml". At column 19, line 66, the patent reads "50 ml" and should read "150 ml". At column 26, line 34, the patent reads "types of occurs" and should read "types of release are possible in these systems. Release by diffusion occurs".

Signed and Sealed this

Twentieth Day of September, 1994

BRUCE LEHMAN

*Attest:*

*Attesting Officer*      *Commissioner of Patents and Trademarks*